United States Patent [19]

Patwardhan et al.

[11] Patent Number: 5,741,304
[45] Date of Patent: Apr. 21, 1998

[54] MULTIDIRECTIONAL ECG COHERENT OPTIMAL TIMING OF DEFIBRILLATION SHOCKS

[75] Inventors: Abhijit R. Patwardhan; Fabio M. Leonelli, both of Lexington, Ky.

[73] Assignee: University of Kentucky Research Foundation, Lexington, Ky.

[21] Appl. No.: 544,301

[22] Filed: Oct. 17, 1995

[51] Int. Cl.$^6$ ............................. A61N 1/39; A61B 5/046
[52] U.S. Cl. ................................... 607/5; 128/705
[58] Field of Search .................... 128/705, 699; 607/5

[56] References Cited

U.S. PATENT DOCUMENTS

| 5,046,504 | 9/1991 | Albert et al. | 128/705 |
| 5,077,667 | 12/1991 | Brown et al. | 128/705 |

OTHER PUBLICATIONS

Peng–Wie Hsia et al., "Genesis of Sigmoidal dose–Response Curve During Defibrillation . . . ", PACE, vol. 13, pp. 1326–1342, Oct. 1990.
Witkowski et al., "Activation Patterns During Ventricular Fibrillation", New York Academy of Sciences, pp. 219–231.
Ravelli et al., "Complex Dynamics Underlying the Human Electrocardiogram", Biological Cybernetics, Biol. Cybern 67, 57–65 (1992).
Bayly et al., "A Quantitative Measurement of Spatial Order in Ventricular Fibrillation", Journal of Cardiovascular Electrophysiology, vol. 4, No. 5, Oct. 1993.
Zipes, "Electrophysiological Mechanism Involved in Ventricular Fibrillation", Mechanisms in Ventricular Fibrillation, Supplement III to Circulation, vols. 51 and 52, Dec. 1975.
Thakor et al., "Adaptive Coherence Analysis of Brain's Nonlinear Response to Injury", The John Hopkins University School of Medicine, pp. 346–347.
Damle et al., "Spatial and Temporal Linking of Epicardial Activation Directions During Ventricular Fibrillation in Dogs", Curculation vol. 86, No. 5, Nov. 1992.
Gliner et al., "The Defibrillation Success Rate Versus Energy Relationship: Part I–Curve Fitting . . . ", Pace, vol. 13, pp. 326–338, Mar. 1990.
Singer et al., "Defibrillation Threshold: Clinical Utility and Therapeutic Implications", Pace, vol. 15, pp. 932–949, vol. 15, Jun. 1992.
Venditti et al., "Rise in Chronic Defibrillation Thresholds in Nonthoracotomy Implantable Defibrillator", pp. 216–223.
Jones et al., "Ventricular Fibrillation: The Importance of Being Coarse?", J. Electrocardiology 17(4), 1984, 393–400.
Carlisle, et al., "Fourier Analysis of Ventricular Fibrillation and Synchronization of DC Countershocks in Defibrillation", Journal of Electrocardiology, 21 (4), 1988, 337–343.
Kuelz et al., Integration of Absolute Ventricular Fibrillation Voltage Correlates with Successful Defibrillation, IEEE Transactions on Biomedical Engineering, vol. 41, No. 8, Aug. 1994, pp. 782–791.
Hsia et al., Genesis of Sigmoid Dose–Response Curve During Defibrillation by Random Shock., PACE, vol. 13, Oct. 1990, pp. 1326–1342.
Ropella et al., "The Coherence Spectrum", Circulation, vol. 80, No. 9, Jul. 1989, p. 112.

*Primary Examiner*—William E. Kamm
*Assistant Examiner*—George R. Evanisko
*Attorney, Agent, or Firm*—Lowe, Price, LeBlanc & Becker

[57] ABSTRACT

A method for of delivering a defibrillation shock to a heart at an optimal time to stop ventricular fibrillation which involves obtaining an electrocardiogram of a heart in at least two directions, determining a time-coherency of the electrocardiogram based upon each of the at least two directions, and computing a tracking function from the time-coherency. An optimal time to apply a defibrillation shock to the heart is determined by locating a local maximum on the tracking function. The method utilizes spacia characteristics of the ventricular fibrillation. The method can be incorporated into implantable cardioverter defibrillators utilizing existing hardware technology.

11 Claims, 3 Drawing Sheets

MULTIDIRECTIONAL ECG COHERENT OPTIMAL TIMING OF DEFIBRILLATION SHOCKS

TECHNICAL FIELD

The present invention relates to ventricular fibrillation. More particularly, the present invention relates to a method of timing the delivery of defibrillation shocks delivered to the heart in order to increase the probability of successful termination of ventricular fibrillation.

BACKGROUND ART

Ventricular fibrillation is the leading cause of death in the United States. If left untreated, ventricular fibrillation is almost always fatal. However, delivering an electric shock to the heart can terminate fibrillation.

Development of sophisticated devices to detect and terminate ventricular fibrillation (VF) such as implantable cardioverter defibrillators (ICD's) is aiding in prevention of death due to VF and prolonging life. With the advent of these devices it has become important to develop mathematical techniques that detect VF with great sensitivity and specificity, and that help deliver defibrillation shocks in an optimal fashion.

Electrical activity during VF is fractionated and unorganized. Some investigators have described VF as a random phenomenon (Hsia P. W., and R. Mahmud. Genesis of sigmoidal dose-response curve during defibrillation by random shock: A theoretical model based on experimental evidence for a vulnerable window during ventricular fibrillation. *PACE* 13: 1326–1342, 1990; and Witkowski F. X. and P. A. Penkoske. Activation patterns during ventricular fibrillation. *Annals New York Acad. of Sci.*, 219–231, 1991), while others have used non-linear, low (Ravelli F. and R. Antolini. Complex dynamics underlying the human electrocardiogram. *Biol. Cybern.* 67: 56–65, 1992), or high order (Bayly P. V., E. E. Johnson, P. D. Wolf, H. S. Greenside, W. M. Smith and R. E. Ideker. A quantitative measurement of spatial order in ventricular fibrillation. *J. Cardiovas. Electrophysiol.* 4(5): 533–546 1993) chaos to describe VF. Although it is not clear whether the electrical activity during VF is stochastic or deterministic, it appears that a depolarization of a 'critical mass' of (Zipes D. P. Electrophysiological mechanisms involved in ventricular fibrillation. *Circulation.* 51–52 (III):120–130, 1975) myocardial cells is essential to successfully terminate VF. Results from modelling studies (Thakor N. V. and X. Kong. Adaptive coherence analysis of brain's nonlinear response to injury. *Proc. IEEE* 345–347, 1993), and evidence of existence of multiple areas of time-varying local organization (Damle R. S., N. M. Kanaan, N. S. Robinson, Y. Z. Ge, J. J. Goldberger and A. H. Kadish. Spatial and temporal linking of epicardial activation directions during ventricular fibrillation in dogs. *Circulation* 86(5): 1547–1558, 1992) suggest that the number of myocardial cells that are depolarized in synchrony varies as a function of time. Consistent with these observations, defibrillation has been shown to be a probabilistic phenomenon (Gliner B. E., Y. Murakawa and N. V. Thakor. The defibrillation success rate versus energy relationship: Part I—Curve fitting and the most efficient defibrillation energy. *PACE* 13: 326–338, 1990; Hsia P. W. et al *PACE* 13: 1326–1342, 1990). That is, at a given energy level of defibrillation (DF) shock, the probability of successfully terminating the VF can be reliably estimated (Gliner B. E. et al, *PACE* 13: 326–338, 1990), while the outcome of a specific DF shock can be uncertain. The shock energy versus probability of success function has been shown to be sigmoidal (Gliner B. E. et al, *PACE* 13: 326–338, 1990), which implies that, up to a certain limit, one could increase the shock energy in order to increase the probability of successful termination of VF. This course of action is probably not desirable, because of the damage to the myocardium due to excessive energy discharges (Singer, I. and D. Lang. Defibrillation threshold: Clinical utility and therapeutic implications. *PACE* 15: 932–950, 1992) and also because of the increased propensity of the myocardium to undesirable arrhythmias after excessive energy discharges (Singer, I. and D. Lang. Defibrillation threshold: Clinical utility and therapeutic implications. *PACE* 15: 932–950, 1992). Moreover, recent investigations (Venditti F. J., D. T. Martin, G. Vassolas and S. Bowen. Rise in chronic defibrillation thresholds in nonthoracotomy implantable defibrillator. *Circulation.* 89:216–223, 1994) suggest that in case of implanted devices, the probability of success for a given energy level might decrease with time.

The concept, that because myocardial electrical organization changes as a function of time during VF, one could use the measured electrical activity to 'time' the delivery of electrical shocks to increase the probability of success, or to classify a VF episode as being more or less amenable to termination, is not new.

In terms of classifying VF episodes, it had been hypothesized (Jones D. L., and G. J. Klein. Ventricular fibrillation: The importance of being coarse? *J. Electrocard.* 17(4) :393–400, 1984) that the "coarse" or higher voltage VF will be easier to terminate than the "fine" or lower voltage VF, however no significant differences between the ability to terminate 'coarse' or 'fine' VF were observed (Jones D. L. et al, *J. Electrocard.* 17(4):393–400, 1984). In terms of timing the delivery of DF shocks, Mower et al. (Mower M. M., Mirowski M. Reid P. R. Synchronization of low energy pulses to rapid deflection signals as a possible mechanism of subthreshold ventricular defibrillation. *Circulation.* 66(II) :71–75, 1982) observed that the DF shocks were more effective when delivered during rapid changes in endocardial electrocardiogram (ECG), however, Hsia et al. (Hsia P. W. et al, *PACE* 13: 1326–1342, 1990) failed to reproduce the observations of Mower et al. Carlisle et al. (Carlisle E. J. F., J. D. Allen, A. Bailey, W. G. Kernohan, J. Anderson and A. A. J. Adgey. Fourier analysis of ventricular fibrillation and synchronization of DC countershocks in defibrillation. *J. Electrocard.* 21(4):337–343, 1988) observed that there was no correlation between the outcome of a DF shock and the time of delivery. The outcome appeared to be independent whether the shocks were delivered at the peaks, troughs or were delivered un-synchronized with the surface ECG measured in a single direction (lead II). Hsia et al. (Hsia P. W. et al, *PACE* 13: 1326–1342, 1990), in a more recent study observed, however, that when the shocks were delivered at the peaks of the absolute voltage of the surface ECG, the probability of success for a shock was higher. Hsia et al. argued that their results were consistent with those of Carlisle et al., because it was not the peaks (positive), or troughs (negative) but the absolute value of voltage at the time of delivery of shocks that determined its outcome.

It is uncertain that the explanation provided by Hsia et al. accounts for the differences in these observations, clearly, the shocks synchronized at the peaks or troughs were synchronous with relatively higher absolute values than those shocks that were un-synchronized. If absolute values determined the outcome of a DF shock, then Carlisle et al. should have observed significant differences in the outcomes of DF shocks between un-synchronized and those synchronized with either the peaks or the troughs. Hsia et al. and Carlisle et al. based their analysis on local behavior of Lead II ECG. Hsia et al. used the absolute values of the last sample of VF before the shock, and Carlisle et al. used the local peaks and valleys for synchronization. It is likely, hence, that their results could have been influenced by random noise that will be present in recorded surface ECG irrespective of whether underlying VF is random or deterministic. Furthermore, the use of ECG measured in a single direction utilizes temporal information only and does not fully utilize spacia characteristics of the ventricular fibrillation.

DISCLOSURE OF THE INVENTION

It is accordingly on object of the present invention to provide a method of determining the optimal time for delivering defibrillation shocks to the heart in order to increase the probability of successful termination of ventricular fibrillation.

Another object of the present invention is to provide a method of timing the delivery of defibrillation shocks delivered to the heart in order to increase the probability of successful termination of ventricular fibrillation.

It is a further object of the present invention to provide a method of utilizing multidirectional ECG's to determine the optimal time for delivering defibrillation shocks to the heart in order to increase the probability of successful termination of ventricular fibrillation.

It is a further object of the present invention to provide an implantable device which times the delivery of defibrillation shocks delivered to the heart in order to increase the probability of successful termination of ventricular fibrillation.

According to these and further objects of the invention which will become apparent as the description thereof proceeds, there is provided a method of determining an optimal time to apply a defibrillation shock to a heart which involves the steps of:

obtaining an electrocardiogram of a heart in at least two directions;
  determining a time-coherency of the electrocardiogram based upon each of the at least two directions;
  computing a tracking function from the time-coherency; and
  locating a local maximum of the tracking function which represents an optimal time to apply a defibrillation shock to the heart.

The present invention also provides a method of delivering a defibrillation shock to a heart at an optimal time to stop ventricular fibrillation which involves the steps of:

obtaining an electrocardiogram of a heart in at least two directions;
  determining a time-coherency of the electrocardiogram based upon each of the at least two directions;
  computing a tracking function from the time-coherency;
  locating a local maximum of the tracking function which represents an optimal time to apply a defibrillation shock to the heart; and
  applying a defibrillation shock to the heart at the optimal time represented by the local maximum of the tracking function.

The present invention further provides an improvement to implantable cardioverter defibrillators having means to detect ventricular fibrillation and to apply a defibrillation shock to a heart, the improvement involving means to:

obtain an electrocardiogram of a heart in at least two directions;
  determine a time-coherency of the electrocardiogram based upon each of the at least two directions;
  compute a tracking function from the time-coherency;
  locate a local maximum of the tracking function which represents an optimal time to apply a defibrillation shock to the heart; and
  apply a defibrillation shock to the heart at the optimal time represented by the local maximum of the tracking function.

BRIEF DESCRIPTION OF DRAWINGS

The invention will be described with reference to the annexed drawings which are presented as non-limiting examples only, in which.

BEST MODE FOR CARRYING OUT THE INVENTION

The present invention is directed to a novel process which computes indices of the organization of myocardial electrical activity during ventricular fibrillation (VF) by analyzing electrocardiograms (ECG) recorded in multiple directions. These indices, which are based on the analysis of electrical activity of the fibrillating ventricle, can be used to develop strategies for "timing" the delivery of defibrillation shocks, such that the chances of successfully terminating fibrillation with minimum energy are maximized. The importance of being able to defibrillate with minimum energy is twofold: 1) Damage to the heart which can occur due to excessive energy discharges would be minimized and 2) With minimum energy required at each shock, the period between battery replacements for an implantable device would be prolonged, or for the same replacement period, the device could be made smaller.

The hypothesis underlying the present invention is that for a given energy level, the probability of success for a defibrillation shock would be higher, if delivered within a time window during a ventricular fibrillation episode, when relatively higher percentage of myocardial cells are depolarized in synchrony.

The present invention involves computation of a 'probability of success' tracking function from the electrical activity (ECG) measured in multiple directions during ventricular fibrillation (VF). The tracking function is used to define "time windows of opportunity" to deliver defibrillation shocks. The "time windows of opportunity" are those times when the probability of successful termination of ventricular fibrillation is a maximum. That is, it is expected that the probability of successfully terminating VF will be higher for those shocks that are delivered during a time window of opportunity defined by the tracking function than those that are delivered otherwise. The time windows of opportunity correspond to instances in which a relatively higher percentage of myocardial cells are depolarized in synchrony.

Features and characteristics of the present invention will be further understood from the following non-limiting example.

EXAMPLE

In this example canine ECG's were recorded in three mutually perpendicular directions (Sagittal S, Transverse T, and Longitudinal L) during repeated trials of electrically induced ventricular fibrillation which was followed by the delivery of a defibrillation shock of a strength (energy) that was known to produce 50% probability of success (i.e. each shock had a 50% chance of either successfully terminating the VF or failing to terminate the VF). An up-down search method was employed to establish a defibrillation threshold (DFT) for each animal, i.e. energy level of the DS that produces 50% probability of success. Those shocks that failed to terminate VF were followed by a 'rescue' shock. Data were collected from one canine during 20 trials of VF.

Figure 1:
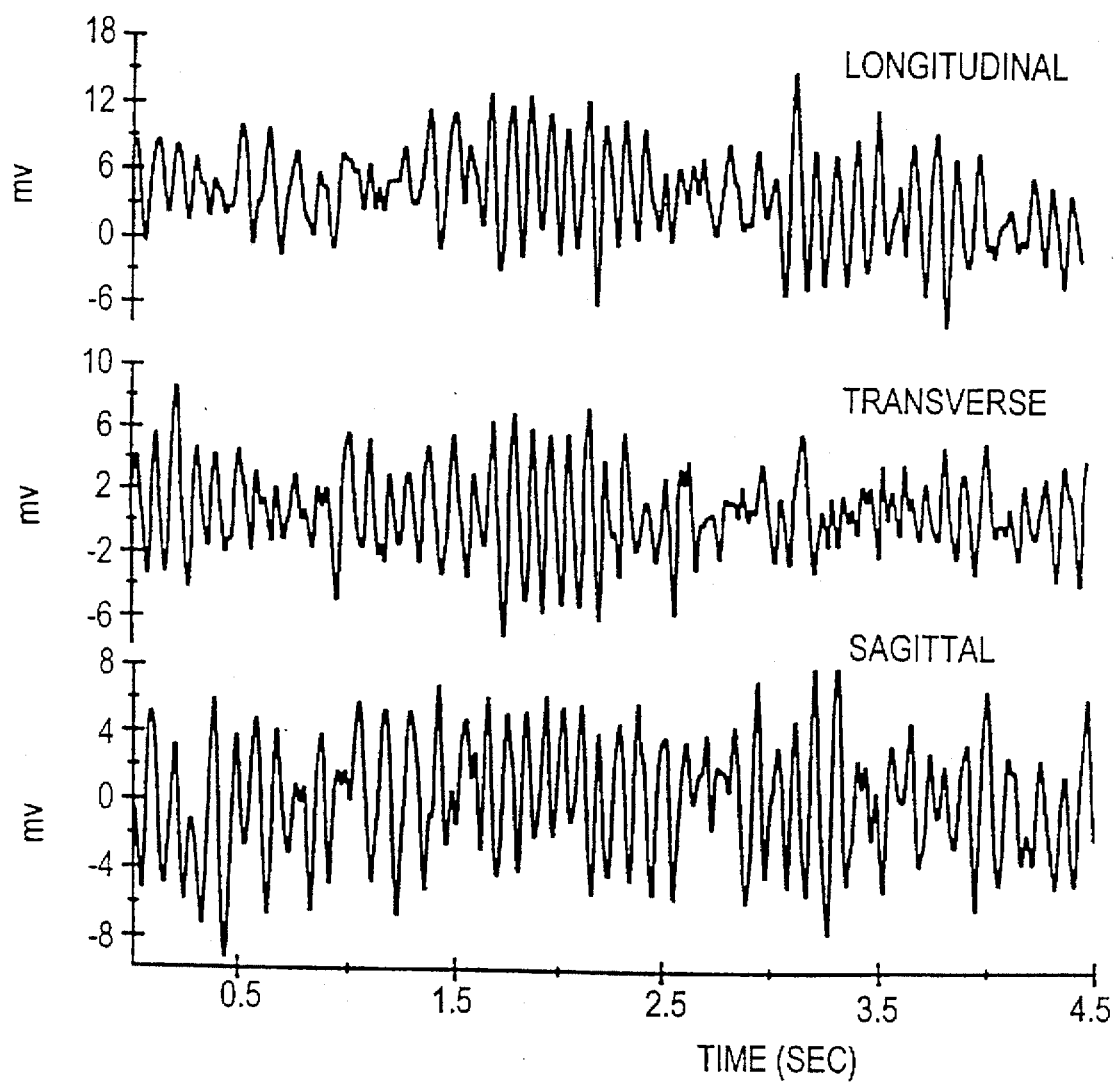
FIG. 1 is an orthogonal electrocardiogram of ventricular fibrillation in the sagittal, longitudinal, and transverse directions.

FIG. 1 shows the orthogonal ECG recorded during 5 seconds of VF during one trial. The ECG in FIG. 1 were recorded at a rate of 2000 samples/second in the sagittal (X), longitudinal (Y), and transverse (Z) directions.

From the orthogonal ECG recordings during VF prior to and up to the time of delivery of DS, indices were computed using analysis of time-coherence estimates between the three electrograms, xy, yz, and xz, and the phase relationships between x and yz, y and xz, and z and xy. These analyses were selected to indicate the cohesiveness of the relationships over time between the electrical measurements made in three mutually perpendicular directions. Higher degree of cohesiveness indicate higher degree of organization, and higher probability of successful defibrillation.

Figure 2:
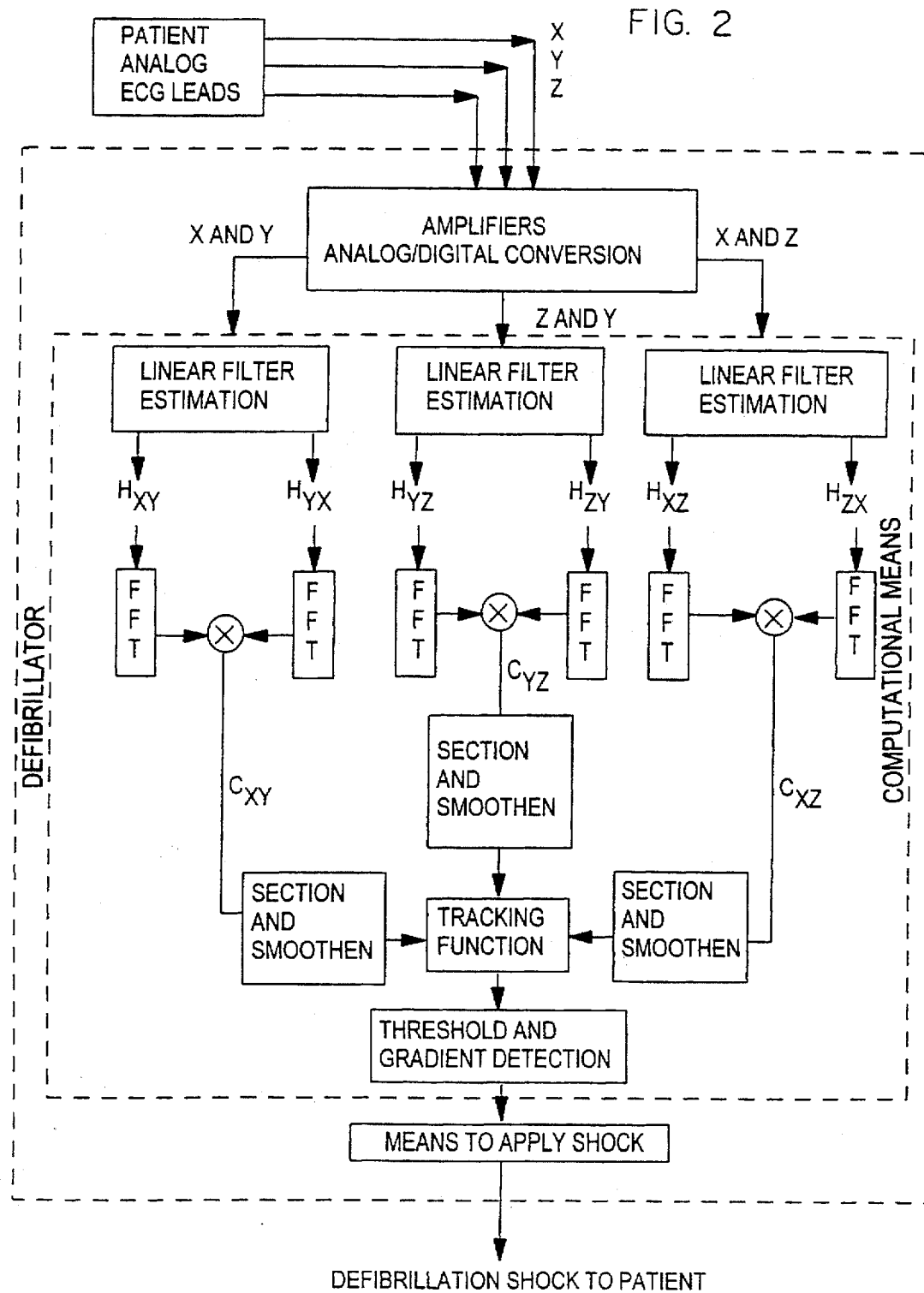
FIG. 2 is a time-coherence estimator network used for the computation of time-coherencies between electrocardiograms recorded in three directions according to the present invention.

Computation of the tracking function was performed using time-coherencies which were estimated using the network shown in FIG. 2. Although the tracking function was computed using mutually orthogonal ECG in this example, it is not necessary to have 3 ECG measurements in orthogonal directions. According to the present invention, the tracking function can be determined from ECG measured in at least two different directions.

The coherence between pairs of ECG were computed from the Fourier Transforms of the linear filters $H_{xy}$ (where H represents the dynamics between the input x and the output y), using the equations given below. The filters were adapted in time using a least mean square (LMS) error algorithm. For example, for any pair of $ECG_{xy}$, the tracking function was computed as follows:

Step 1: Estimation of ECG in y direction using filter $H_{xy}$, and M measurements of ECG in x direction were made using the following equation:

$$y'(k)=H^T_{xy}(k)X(k),$$

where y'(k) is the estimated ECG in the y direction at time instant k, and X(k) is the measured ECG vector in the x direction at time instant k, while $H_{xy}$ is the estimation filter that predicts ECG in direction y based on ECG measured in direction x.

Step 2: $H_{xy}$ was adaptively updated using the least means square rule as follows:

$$H_{xy}(k+1)=H_{xy}(k)+\mu_x\{y(k)-y'(k)\}X(k)$$

where $\mu_x$ is the adaptation constant and y(k) is the measured ECG in the y direction.

Step 3: The coherence at time instant k was estimated using the frequency domain representation of filters $H_{xy}$ and $H_{yx}$ as follows:

$$C_{xy}(f,k)=H'_{xy}(f,k)H'_{yx}(f,k)$$

where f is the frequency parameter.

Step 4: The tracking function O(k) was computed as follows:

$$O(k)=\alpha_{xy}Y_{xy}+\alpha_{yz}Y_{yz}+\alpha_{xz}Y_{xz}$$

where, $$Y_{ab}(k) = \sum_{f\in\Omega} \sum_{\tau\in\Phi} C_{ab}(f,\tau)\omega(\tau)$$

and $\alpha_{ab}$ are the weights associated with each pair of ECG measurements (shown in the equation above are ECG pairs XY, YZ and ZX).

The parameters $\Omega$ and $\Phi$ determine the coherence frequency bandwidth contribution to the tracking function and the degree of time smoothing of the tracking function. $\omega(\tau)$ is the time smoothing window function.

Figure 3:
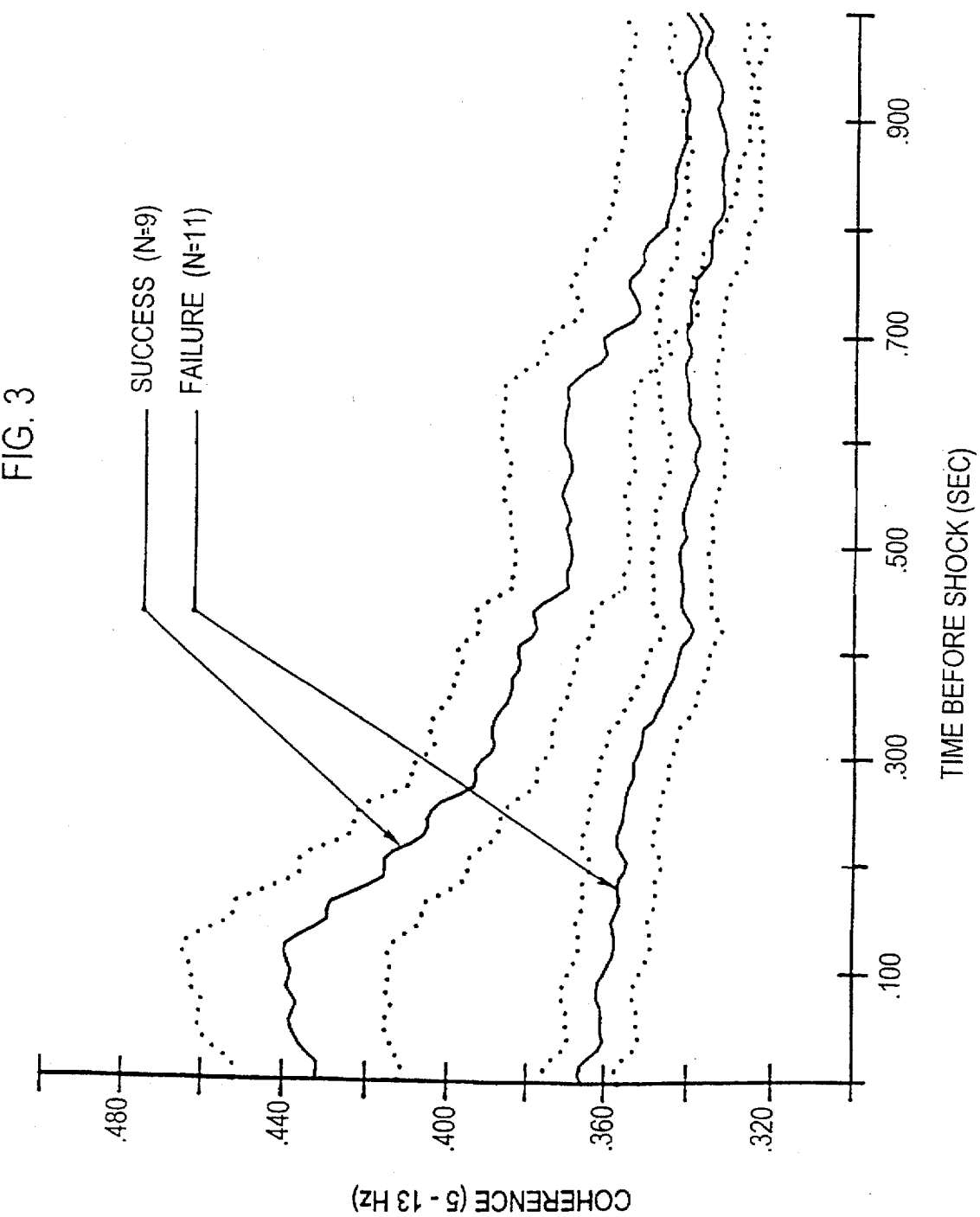
FIG. 3 is a plot showing the probability of success tracking function computed from electrocardiograms recorded in the sagittal and longitudinal planes.

FIG. 3 shows the averaged (±1 standard deviation, dotted line) tracking function computed from 20 trials conducted in this example (9 success and 11 failures) in the Sagittal-Longitudinal (SL) plane. All 20 trials were conducted with the same shock energy (17 J), with shocks delivered between right ventricular apex (RVA) and a subcutaneous patch (SP).

The tracking function was computed with $\alpha SL=1$ and $\alpha_{TL}$, $\alpha_{ST}=0$. FIG. 3 shows that on average the value of the tracking function O(k) was higher for those trails that were successful than for those that were failures. This implies that if the shocks are 'timed' to occur when the on-line estimates of O(k) are above a preset threshold and are at a local maximum (as determined by estimation of gradient of O(k) and gradient of the gradient of O(k)), the probability of successful termination of VF would be increased.

The present invention is based on the theory that during certain time windows within a VF episode, there will be more organization of electrical activity relative to other times, and hence, the coherence and the phase coupling between the three electrograms will be higher. The inventors have used non-parametric (pseudo-Wigner distributions) and parametric modelling (recursive prediction error method) to estimate time-coherency spectra. Estimates of the degree of nonlinear phase coupling between electrograms are computed using bi-spectrum and bi-coherence. These higher order spectral estimates are computed using a non-parametric method. The time-coherency and bi-spectral surfaces can be integrated in frequency and averaged over time, or integrated within certain frequency areas to yield quantitative estimates of electrical organization. The lowest frequency ranges that adequately discriminate between success and failures can be selected because of the computational constraints that will dictate the development of real-time on-line versions of the algorithms.

Time-global average values (computed over the entire VF episode), and time-local average values (computed just before DS, over an interval shorter than the minimum refractory period of myocardial cells) of these indices can be computed. The average values can be used in a linear discriminant function to determine which indices are more sensitive in achieving classification between success and failures. Successful trials will have: a) higher values of time-local averages (relative to failures), which would indicate the presence of 'time windows of opportunity' within a given VF episode when the myocardium is more amenable to defibrillation, and/or b) higher values of time-global averages, which would indicate that some VF episodes are more amenable to defibrillation than others.

The computational and memory hardware requirements necessary to perform the above steps of optimal delivery of shocks are well within the limits of existing technology. Accordingly, the process described above can be easily incorporated into existing designs of implantable cardioverter defibrillators (ICD's). For example, the necessary logic circuit to perform the necessary calculations can be readily incorporated into a chip design which in turn can be incorporated into existing ICD's.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A method of determining an optimal time to apply a defibrillation shock to a heart which comprises the steps of:
    obtaining an electrocardiogram of a heart in at least two directions;
    determining a time-coherency of said electrocardiogram based upon each of said at least two directions;
    computing a tracking function from said time-coherency; and
    locating a local maximum of said tracking function which exceeds a preset defibrillation threshold, which local maximum represents an optimal time to apply a defibrillation shock to said heart; and
    delivering a defibrillation shock to the heart at said optimal time.

2. A method of determining an optimal time to apply a defibrillation shock to a heart according to claim 1, wherein said at least two directions comprise orthogonal directions.

3. A method of determining an optimal time to apply a defibrillation shock to a heart according to claim 1, wherein said at least two directions comprise three directions.

4. A method of determining an optimal time to apply a defibrillation shock to a heart according to claim 3, wherein said three directions are orthogonal.

5. A method of determining an optimal time to apply a defibrillation shock to a heart according to claim 1, comprising performing said steps with an implantable cardioverter defibrillator.

6. A method of delivering a defibrillation shock to a heart at an optimal time to stop ventricular fibrillation which comprises the steps of:
    obtaining an electrocardiogram of a heart in at least two directions;
    determining a time-coherency of said electrocardiogram based upon each of said at least two directions;
    computing a tracking function from said time-coherency;
    locating a local maximum of said tracking function which exceeds a preset defibrillation threshold, which local maximum represents an optimal time to apply a defibrillation shock to said heart; and
    applying a defibrillation shock to said heart at said optimal time represented by said local maximum of said tracking function.

7. A method of determining an optimal time to apply a defibrillation shock to a heart according to claim 6, wherein said at least two directions comprise orthogonal directions.

8. A method of determining an optimal time to apply a defibrillation shock to a heart according to claim 6, wherein said at least two directions comprise three directions.

9. A method of determining an optimal time to apply a defibrillation shock to a heart according to claim 8, wherein said three directions are orthogonal.

10. A method of determining an optimal time to apply a defibrillation shock to a heart according to claim 6, comprising performing said steps with an implantable cardioverter defibrillator.

11. In an implantable cardioverter defibrillator having means to detect ventricular fibrillation and to apply a defibrillation shock to a heart, the improvement comprising means to:
    obtain an electrocardiogram of a heart in at least two directions;
    determine a time-coherency of said electrocardiogram based upon each of said at least two directions;
    compute a tracking function from said time-coherency;
    locate a local maximum of said tracking function which exceeds a preset defibrillation threshold, which local maximum represents an optimal time to apply a defibrillation shock to said heart; and
    apply a defibrillation shock to said heart at said optimal time represented by said local maximum of said tracking function.

* * * * *